(12) United States Patent
Wallnewitz et al.

(10) Patent No.: US 8,485,189 B2
(45) Date of Patent: Jul. 16, 2013

(54) BREATHING MASK

(75) Inventors: Oliver Wallnewitz, Lübeck (DE); Ludger Tappehorn, Lübeck (DE); Ines Materna, Wedendorf (DE)

(73) Assignee: Dräger Medical GmbH, Lübeck (DE)

( * ) Notice: Subject to any disclaimer, the term of this patent is extended or adjusted under 35 U.S.C. 154(b) by 593 days.

(21) Appl. No.: 12/767,318

(22) Filed: Apr. 26, 2010

(65) Prior Publication Data

US 2010/0307505 A1 Dec. 9, 2010

(30) Foreign Application Priority Data

Jun. 3, 2009 (DE) .......................... 10 2009 023 664

(51) Int. Cl.
*A61M 11/00* (2006.01)

(52) U.S. Cl.
USPC ................................ 128/206.22; 128/205.27

(58) Field of Classification Search
USPC ............. 128/206.22, 206.19, 205.27, 206.21, 128/205.19, 911, 206.18
See application file for complete search history.

(56) References Cited

U.S. PATENT DOCUMENTS

| | | | | |
|---|---|---|---|---|
| 3,276,445 A | * | 10/1966 | Langdon | 128/206.15 |
| 4,141,703 A | * | 2/1979 | Mulchi | 96/132 |
| 4,361,146 A | * | 11/1982 | Woicke | 128/206.12 |
| 4,846,170 A | * | 7/1989 | McAnalley et al. | 128/207.13 |
| 5,261,893 A | | 11/1993 | Zamierowski | |
| 5,706,804 A | * | 1/1998 | Baumann et al. | 128/206.19 |
| 5,715,814 A | | 2/1998 | Ebers | |
| 5,762,643 A | * | 6/1998 | Ray et al. | 604/383 |
| 6,237,596 B1 | | 5/2001 | Bohmfalk | |
| 6,357,440 B1 | * | 3/2002 | Hansen et al. | 128/206.19 |
| 2005/0051171 A1 | | 3/2005 | Booth | |

FOREIGN PATENT DOCUMENTS

| | | |
|---|---|---|
| CN | 1569283 A | 1/2005 |
| DE | 4425051 | 5/1995 |
| EP | 1835955 A1 | 9/2007 |
| JP | 2002 052 082 A | 2/2002 |
| SU | 627820 | 10/1978 |
| WO | WO 2006069415 A1 | 7/2006 |

* cited by examiner

*Primary Examiner* — Steven Douglas
(74) *Attorney, Agent, or Firm* — McGlew and Tuttle, P.C.

(57) ABSTRACT

A breathing mask is provided which prevents condensation in the interior space of the mask. The mask body (2) is provided in some sections with a material (8) that is waterproof but permeable to water vapor.

20 Claims, 4 Drawing Sheets

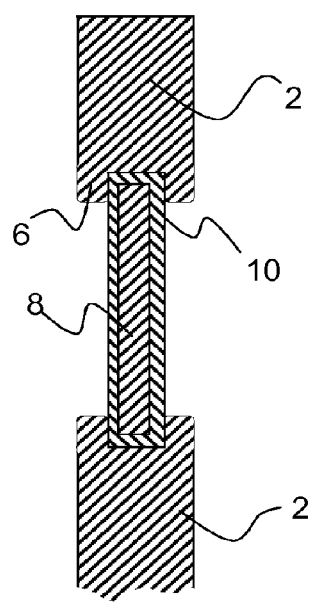
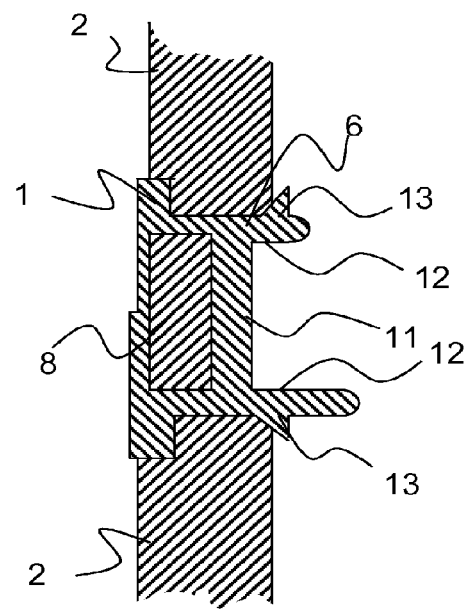
Fig. 3
Fig. 4

BREATHING MASK

CROSS REFERENCE TO RELATED APPLICATIONS

This application claims the benefit of priority under 35 U.S.C. §119 of German Patent Application DE 10 2009 023 664.3 filed Jun. 3, 2009, the entire contents of which are incorporated herein by reference.

FIELD OF THE INVENTION

The present invention pertains to a breathing mask, preferably a breathing mask for medical applications.

BACKGROUND OF THE INVENTION

For respirating (also known as ventilating) a patient, above all for respiration at home, the breathing gas is humidified before it is fed to the patient. Room air is drawn in via a filter and fed to the patient via a humidifier in case of respiration at home, especially for the therapy of sleep apnea. Condensation may now occur in the interior space of the mask, which is perceived by the patient as disturbing if the patient must briefly remove the mask during the night to remove the condensate. Breathing masks that are worn by a patient during sleep are usually used in various positions, corresponding to the individual sleeping habits. High level of sleep comfort must be reached without the patient being disturbed by possible condensation.

A breathing mask in which a heating coil, which heats the mask to prevent condensation is arranged on the outside of the mask body, is known from JP 2002 052 082 A. The drawback of the prior-art mask is that an additional electric line must be led to the mask for operating the heating coil and that overheating of the mask may occur in case of a defect.

SUMMARY OF THE INVENTION

The basic object of the present invention is to improve a breathing mask of this type such that condensation in the interior space of the mask is avoided.

According to the invention, a breathing mask is provided comprising a mask body and material connected to the mask body in at least some sections. The material being waterproof but also permeable to water vapor and forming a vapor passageway to remove moisture from the interior space of the mask.

The material may be connected to the mask body by bonding, pressing or by means of a plug-in frame. The material may be located in openings formed in the mask body.

The material may be attached on an inside of the mask body. The mask body may have a collection space for condensate between the mask body and the material.

The material may be a membrane comprising a textile carrier and a barrier layer. Advantageously the textile carrier may consist of polyester and the barrier layer may consist of polyurethane.

The advantage of the present invention is that moisture is removed from the side of the interior space of the mask facing the patient by means of a material, which is arranged in the area of the mask body and is waterproof, on the one hand, but is permeable to water vapor, on the other hand. Such materials are known from pieces of clothing, where they are used to protect a person from moisture but to make possible the release of body moisture to the environment.

The material is firmly connected to the mask body either by bonding or pressing or it is arranged detachably on the mask body. In case of connection by bonding, it is possible to connect the material directly with the mask body or to insert it into a groove on the mask body.

A plug-in frame for the material is suitable for applications in which replacement of the material is desirable. The material is connected for this to the plug-in frame via a plastic wall extending around the outside of the material and the plug-in frame is inserted into a corresponding opening of the mask body. As an alternative, the material can be fastened in a silicone frame, which is arranged on the mask body with separate fastening means, for example, with magnets.

As an alternative, the material may also be pressed directly into the mask body during the manufacturing process. Openings in the mask body are advantageously suitable for use as fastening points for the material. Either individual, larger openings may be present in the mask body, which are closed with the material, or small perforations are prepared at closely spaced locations from one another in the mask body, which are covered with the material that is in contact on the inside of the mask body. It is also possible as an alternative to press the material directly into the mask body during the manufacturing process, in which case the connection between the inside of the mask and the outside of the mask is established by the openings.

A suitable material in the form of a membrane is available under the name "Klima-PES-Strickware" [climate control polyester knitwear] and consists of the following components:

| textile carrier: | 100% polyester, |
|---|---|
| barrier layer: | 100% polyurethane |

The membrane is resistant to boiling and to disinfectants.

The membrane described has a weight of about 115 $g/m^2$ and a thickness of 0.25 mm. The waterprooofness of the membrane is said to be above 3,000 mm according to DIN EN 20811. The water vapor permeability of the membrane is determined according to DIN 53122 (climate B→38±1° C. and 90±2° relative humidity). The permeability of the membrane is to be related to a period of 24 hours and one square meter of area of the membrane and it thus equals 2,600 $g/m^2d$.

The membrane is absolutely pressure-resistant in the dry state in the case of application, 3-30 mbar. In the wet state, the membrane has a leakage flow of 0.11 L/minute beginning from a respiration pressure of 20 mbar. The leakage flow increases continuously to 0.26 L/minute with increasing respiration pressure (at 30 mbar).

The water vapor permeability at a temperature gradient of 12° C. (21° C. under ambient conditions and 33° C. in the interior space of the mask) is approximately 4,240 $g/m^2d$. The greater the temperature gradient, the more effectively water vapor is removed from the interior space of the mask to the outside.

An exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a longitudinal sectional view through an opening in the mask body;

FIG. 4 is a longitudinal sectional view showing a membrane in a plug-in frame.

DESCRIPTION OF THE PREFERRED EMBODIMENTS

Figure 1:
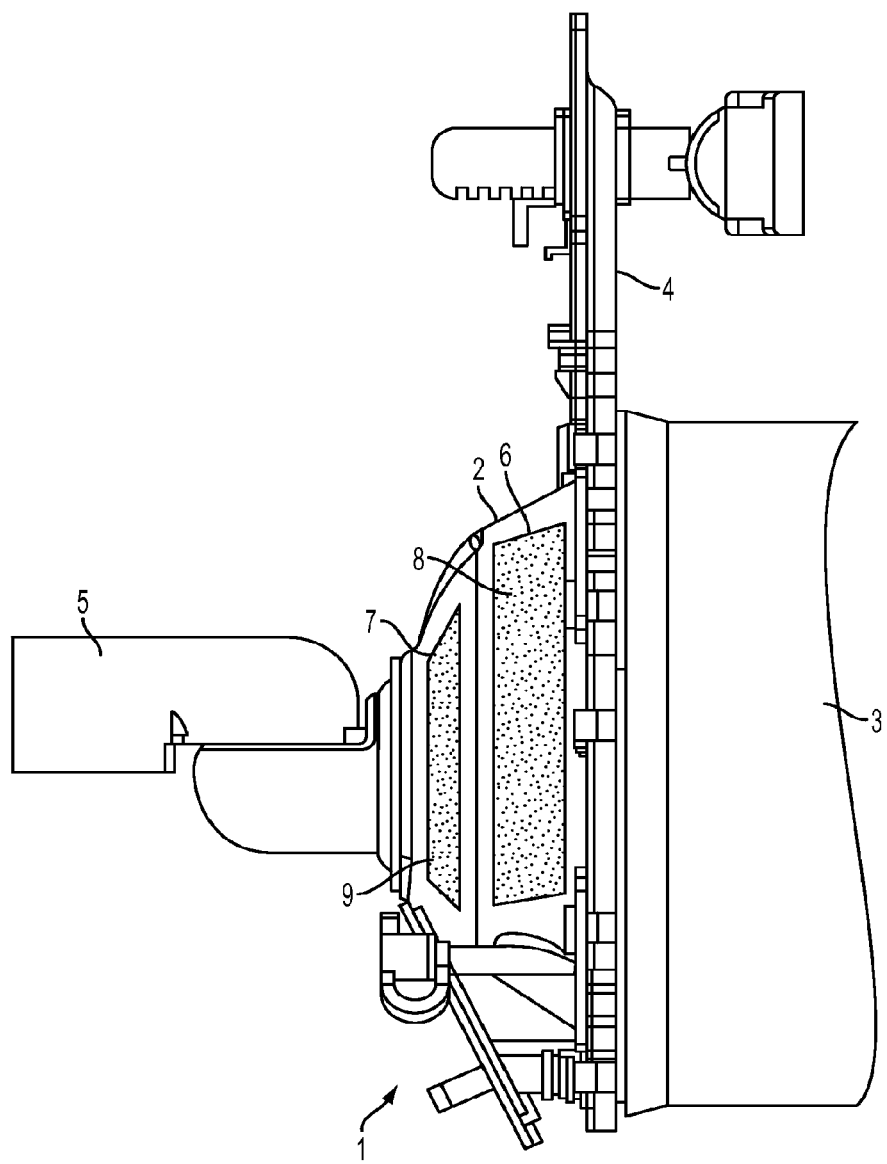
FIG. 1 is a side view of a breathing mask.

Referring to the drawings in particular, FIG. 1 shows a side view of a breathing mask 1 according to the present invention. The breathing mask 1 comprises a mask body 2, a mask pad 3 and a head rest 4. Breathing gas is sent into the interior space of the breathing mask 1 via an angle piece 5. The mask body 2 has openings 6, 7, which are closed with a membrane 8, 9, which is waterproof but permeable to water vapor. Corresponding openings closed with membranes, which are not shown in FIG. 1 for the sake of greater clarity, are likewise provided on the opposite side of the mask body 2.

Figure 2:
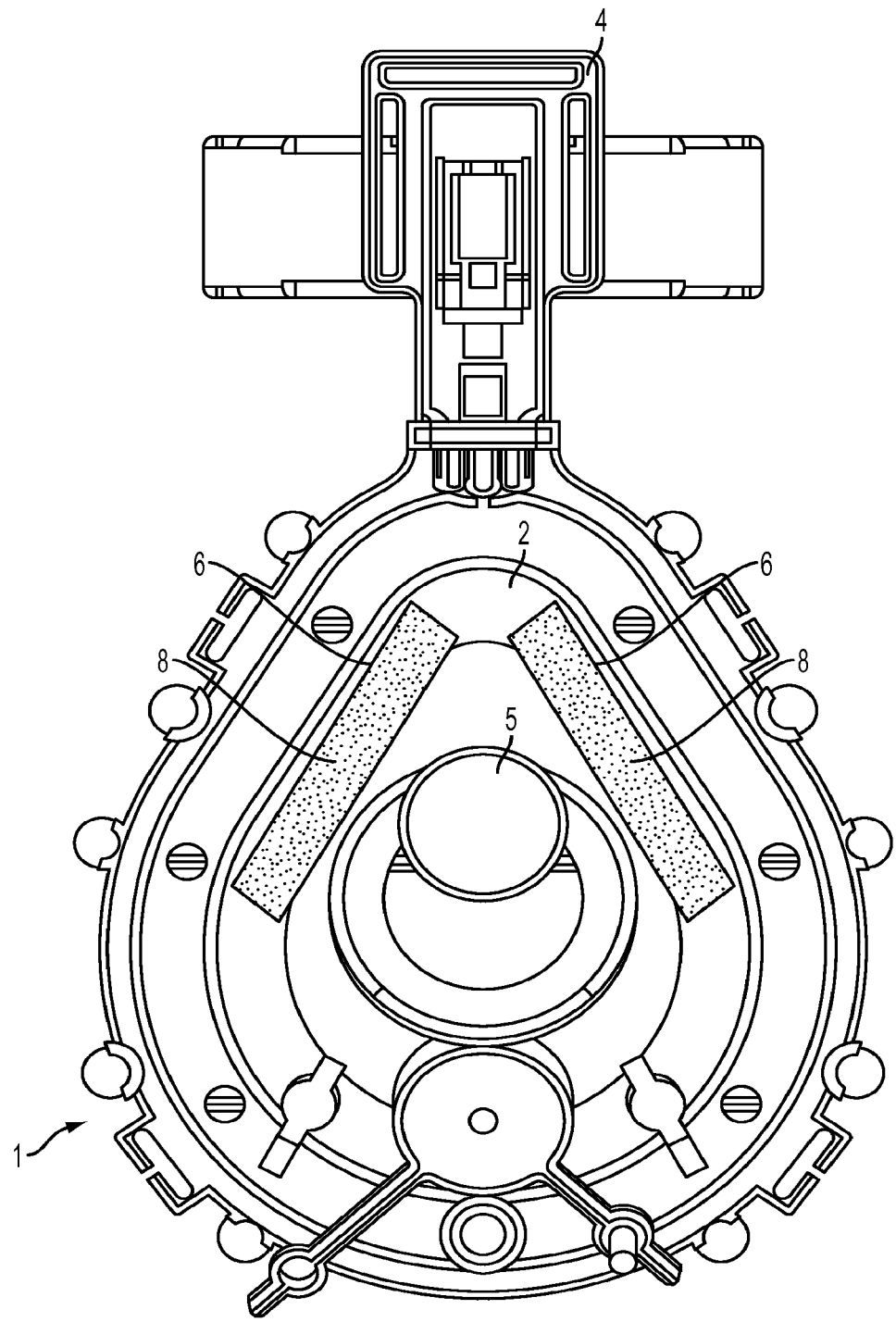
FIG. 2 is a top view of the breathing mask according to FIG. 1.

FIG. 2 shows a top view of the breathing mask 1 according to FIG. 1 with the openings 6, which are closed with the membranes 8. The openings 7, FIG. 1, which are arranged towards the angle piece 5, are not shown in FIG. 2 for the sake of greater clarity.

FIG. 3 shows in detail the longitudinal section of opening 6 with the membrane 8. Membrane 8 is fastened in an undercut 10 of the mask body 2.

In an alternative embodiment according to FIG. 4, membrane 8 is received in a plug-in frame 11 and is inserted into the opening 6 by means of the plug-in frame 11. On a side facing the interior space of the mask, the plug-in frame 11 has two ejectors 12 of a tongue-like design with projections 13, which are in contact with the inside of the mask body 2. By compressing the ejectors 12, the projections 13 are pressed into the opening 6 and the plug-in frame 11 can be removed from the opening 6 to the outside of the mask body 2.

Figure 5:
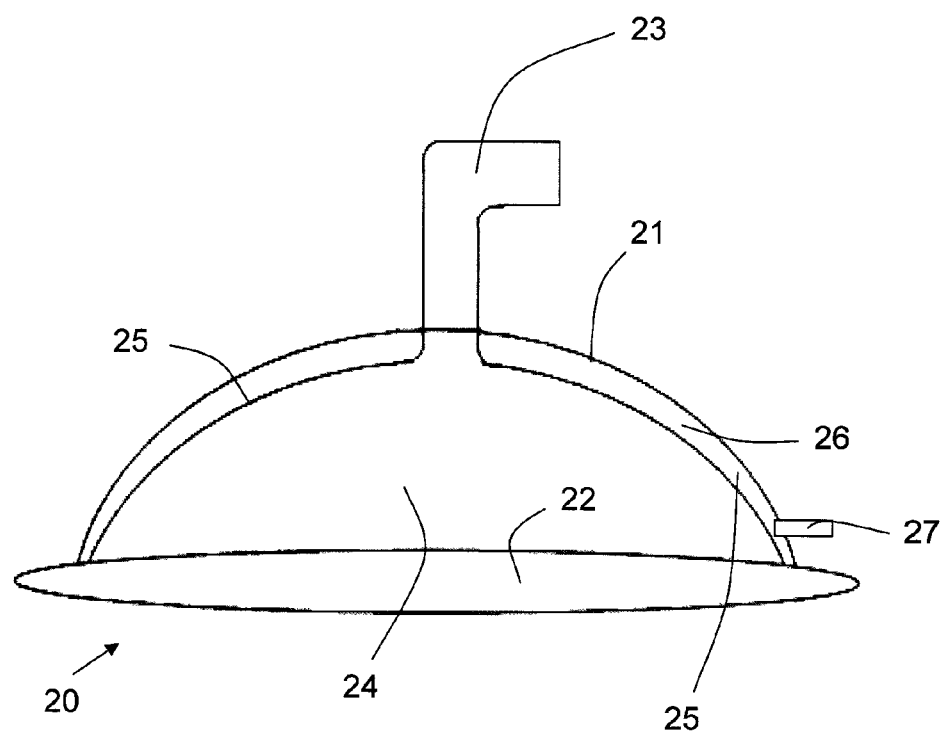
FIG. 5 is an alternative embodiment of a breathing mask.

FIG. 5 shows a schematic view of an alternative embodiment of a breathing mask 20 with a mask body 21, with a mask pad 22 and with an angle piece 23. A membrane 25, which is fastened, on the one hand, circumferentially to the mask pad 22 as well as to the angle piece 23, is arranged in the interior space 24 of the mask. A collection space 26 for separated condensate, which can be drained off via a tube connection 27, is located between the membrane 25 and the mask body 21.

While specific embodiments of the invention have been described in detail to illustrate the application of the principles of the invention, it will be understood that the invention may be embodied otherwise without departing from such principles.

| List of Reference Numbers | |
|---|---|
| 1, 20 | Breathing mask |
| 2, 21 | Mask body |
| 3, 22 | Mask pad |
| 4 | Head rest |
| 5, 23 | Angle piece |
| 6, 7 | Openings |
| 8, 9, 25 | Membrane |
| 10 | Undercut |
| 11 | Plug-in frame |
| 12 | Ejector |
| 13 | Projection |
| 24 | Interior space of mask |
| 26 | Collection space |
| 27 | Tube connection |

What is claimed is:

1. A breathing mask comprising:
a mask body with a moisture passage opening from an interior of the mask body to an exterior of the mask body; and
waterproof and water vapor permeable material connected to the mask body in at least some sections and covering and closing said moisture passage opening, said material being waterproof but also permeable to water vapor to define at least one water vapor passageway, through said moisture passage opening and through said waterproof and water vapor permeable material, from the interior of the mask body to the exterior of the mask body to remove moisture from an interior space of the mask body to the exterior environment of the mask body.

2. A breathing mask in accordance with claim 1, wherein said material is connected to said mask body by bonding, pressing or by means of a plug-in frame.

3. A breathing mask in accordance with claim 1, wherein:
the mask body has at least one additional moisture passage opening to provide moisture passage openings;
said material is located in the moisture passage openings formed in said mask body.

4. A breathing mask in accordance with claim 1, wherein said material is attached on an inside surface of said mask body, said mask body having a collection space for condensate between said mask body and said material.

5. A breathing mask in accordance with claim 1, wherein said material is a membrane comprising a textile carrier and a barrier layer.

6. A breathing mask in accordance with claim 5, wherein said textile carrier consists of polyester and the barrier layer consists of polyurethane.

7. A breathing mask comprising:
a mask body with a mask breathing gas opening defining a breathing gas passage and with a moisture opening defining a passage from a mask interior space to an exterior environment of the mask body; and
material sections connected to said mask body, said material sections comprising waterproof material that is permeable to water vapor, at least one of said material sections covering said moisture opening and closing said moisture opening whereby said mask body with connected material sections allows passage of moisture from the mask interior space of the mask body to the exterior environment of the mask body.

8. A breathing mask in accordance with claim 7, wherein said material sections are connected to said mask body by bonding, pressing or by means of a plug-in frame.

9. A breathing mask in accordance with claim 8, wherein:
said mask body comprises at least one additional moisture opening defining another passage from a mask interior space to an exterior environment of the mask body, whereby said mask body defines a plurality of moisture openings with each of said material sections covering one of said moisture openings.

10. A breathing mask in accordance with claim 7, wherein said material sections are attached on an inside of said mask body, said mask body having a collection space for condensate between said mask body and said material sections.

11. A breathing mask in accordance with claim 9, wherein each of said material sections is a membrane comprising a textile carrier and a barrier layer.

12. A breathing mask in accordance with claim 11, wherein said textile carrier consists of polyester and the barrier layer consists of polyurethane.

13. A breathing mask comprising:
a mask body formed of gas impermeable material defining a mask interior space, said gas impermeable material of said mask body having a mask breathing gas opening forming a breathing gas passage and having plural moisture discharge openings from the mask interior space to an exterior environment of the mask body; and
material sections connected to said mask body, each of said material sections covering one of said plural moisture discharge openings and closing one of said plural moisture discharge openings, each of said material sections comprising waterproof material that is permeable to water vapor, each of said material sections defining a water vapor passageway for passage of moisture from said mask interior space to the exterior environment of the mask body.

14. A breathing mask in accordance with claim 13, wherein each of said material sections is connected to said mask body by bonding each of said material sections to said mask body.

15. A breathing mask in accordance with claim 13, wherein said material sections are connected to said mask body by pressing each of said material sections to said mask body.

16. A breathing mask in accordance with claim 13, further comprising a plurality of plug-in frames, each of said material sections being mounted to one of said plug-in frames and each of said openings defining a plug-in frame receiving portion, wherein each of said plug-in frames with mounted material section is plugged into one of said openings.

17. A breathing mask in accordance with claim 13, wherein each of said material sections is attached on an inside of said mask body, said mask body having a collection space for a collection of condensate, said collection space being disposed between said mask body and said material sections.

18. A breathing mask in accordance with claim 13, wherein each of said material sections is a membrane comprising a textile carrier and a barrier layer.

19. A breathing mask in accordance with claim 18, wherein said textile carrier consists of polyester and the barrier layer consists of polyurethane.

20. A breathing mask in accordance with claim 1, wherein:
said mask body comprises a gas impermeable material forming a mask interior space, said gas impermeable material of said mask body defining a mask breathing gas opening forming a breathing gas passage for breathing gas to enter into the mask interior space and said gas impermeable material of said mask body defining said moisture passage opening.

\* \* \* \* \*